United States Patent [19]

Chang

[11] Patent Number: 5,225,328
[45] Date of Patent: Jul. 6, 1993

[54] STABLE ALKALINE PHOSPHATASE COMPOSITIONS WITH COLOR ENHANCEMENT AND THEIR USE IN ASSAYS

[75] Inventor: Chin-Hai Chang, Los Altos, Calif.

[73] Assignee: Quidel Corporation, San Diego, Calif.

[21] Appl. No.: 707,718

[22] Filed: May 30, 1991

[51] Int. Cl.$^5$ ............................................. C12Q 1/42
[52] U.S. Cl. ................................. 435/7.9; 435/7.92; 435/7.93; 435/18; 435/19
[58] Field of Search ................. 435/7.9, 7.92, 7.93, 435/18, 19

[56] References Cited

U.S. PATENT DOCUMENTS

| | | | |
|---|---|---|---|
| 4,659,657 | 4/1987 | Harnisch | 435/18 |
| 5,035,998 | 7/1991 | Eltz et al. | 435/18 |
| 5,077,198 | 12/1991 | Shih et al. | 435/7.9 |

*Primary Examiner*—Sam Rosen
*Attorney, Agent, or Firm*—Townsend and Townsend Khourie and Crew

[57] ABSTRACT

Methods and compositions for membrane flow-through assays using substrate and enzyme conjugate is described. A preferred method of the present invention comprises providing *E. coli* alkaline phosphatase (ECAP) conjugate, with additional color enhancement provided by combining lithium salt with the substrate, calcium and/or magnesium salts with the conjugate, and polyalcohol polymers with the conjugate. Color development is further enhanced by spotting tetrazolium dyes, such as the Nitro Blue tetrazolium series, onto the membrane.

19 Claims, 6 Drawing Sheets

| I.D. | SPOT | DENSITY | | | | | | | x | S.D. | spot-bkg |
|---|---|---|---|---|---|---|---|---|---|---|---|
| No LiNO3 3 Min. incubation | ref | | | | | | | | --- | --- | -DIV/0! |
| | bkg | 0.9 | 0.91 | 0.89 | | | | | 0.90 | 0.01 | |
| | test | 1.31 | 1.34 | 1.37 | | | | | 1.34 | 0.03 | 0.44 |
| 0.5M LiNO3 1 Min. incubation | ref | | | | | | | | --- | --- | -DIV/0! |
| | bkg | 0.89 | 0.89 | 0.9 | | | | | 0.89 | 0.01 | |
| | test | 1.25 | 1.21 | 1.24 | | | | | 1.23 | 0.02 | 0.34 |
| 1.0M LiNO3 1 Min. incubation | ref | | | | | | | | --- | --- | -DIV/0! |
| | bkg | 0.92 | 0.91 | 0.9 | | | | | 0.91 | 0.01 | |
| | test | 1.47 | 1.45 | 1.41 | | | | | 1.44 | 0.03 | 0.53 |
| 1.5M LiNO3 1 Min. incubation | ref | | | | | | | | --- | --- | -DIV/0! |
| | bkg | 0.89 | 0.89 | 0.9 | | | | | 0.89 | 0.01 | |
| | test | 1.46 | 1.57 | 1.46 | | | | | 1.48 | 0.03 | 0.58 |
| | ref | | | | | | | | --- | --- | -DIV/0! |
| | bkg | | | | | | | | --- | --- | |
| | test | | | | | | | | --- | --- | -DIV/0! |
| | ref | | | | | | | | --- | --- | -DIV/0! |
| | bkg | | | | | | | | --- | --- | |
| | test | | | | | | | | --- | --- | -DIV/0! |

FIG. 4.

| I.D. | SPOT | DENSITY | | | | | | | x | S.D. | spot-bkg |
|---|---|---|---|---|---|---|---|---|---|---|---|
| Std. Substrate without LiNO3 1 min. incubation | ref | | | | | | | | --- | --- | -DIV/0! |
| | bkg | 0.9 | 0.91 | 0.91 | 0.91 | 0.9 | 0.89 | 0.92 | 0.91 | 0.01 | |
| | test | 1.05 | 1.11 | 1.08 | 1.09 | 1.06 | 1.02 | 1.06 | 1.07 | 0.03 | 0.16 |
| Std Substrate with 1.5M LiNO3 1 min. incubation | ref | | | | | | | | --- | --- | -DIV/0! |
| | bkg | 0.89 | 0.9 | 0.91 | 0.9 | 0.9 | 0.89 | 0.90 | 0.90 | 0.01 | |
| | test | 1.74 | 1.72 | 1.71 | 1.66 | 1.78 | 1.74 | 1.71 | 1.72 | 0.04 | 0.82 |
| | | 0.82/0.16 = 512% | | | | | | | --- | --- | -DIV/0! |
| | | | | | | | | | --- | --- | |
| | | | | | | | | | --- | --- | -DIV/0! |

FIG. 5.

| I.D. | SPOT | DENSITY | | | x | S.D. | spot-bkg |
|---|---|---|---|---|---|---|---|
| Mg Chloride 0 | ref | --- | | | --- | --- | -DIV/0! |
| | bkg | 0.93 | 0.91 | 0.92 | 0.92 | 0.01 | |
| | test | 1.18 | 1.16 | 1.25 | 1.20 | 0.05 | 0.28 |
| 0.062M | ref | --- | | | --- | --- | -DIV/0! |
| | bkg | 0.92 | 0.92 | 0.91 | 0.92 | 0.01 | |
| | test | 1.53 | 1.52 | 1.46 | 1.51 | 0.03 | 0.59 |
| 0.125M | ref | --- | | | --- | --- | -DIV/0! |
| | bkg | 0.92 | 0.91 | 0.91 | 0.91 | 0.01 | |
| | test | 1.42 | 1.61 | 1.48 | 1.50 | 0.10 | 0.59 |
| 0.25M | ref | --- | | | --- | --- | -DIV/0! |
| | bkg | 0.93 | 0.91 | 0.9 | 0.91 | 0.02 | |
| | test | 1.5 | 1.68 | 1.63 | 1.60 | 0.09 | 0.69 |
| 0.5M | ref | --- | | | --- | --- | -DIV/0! |
| | bkg | 0.93 | 0.91 | 0.92 | 0.92 | 0.01 | |
| | test | 1.79 | 1.53 | 1.52 | 1.61 | 0.15 | 0.69 |
| 1M | ref | --- | | | --- | --- | -DIV/0! |
| | bkg | 0.93 | 0.92 | 0.92 | 0.92 | 0.01 | |
| | test | 1.87 | 1.83 | 1.82 | 1.84 | 0.03 | 0.92 |
| Ca Chloride 0 | ref | --- | | | --- | --- | -DIV/0! |
| | bkg | 0.91 | 0.92 | 0.91 | 0.91 | 0.01 | |
| | test | 1.12 | 1.14 | 1.18 | 1.15 | 0.03 | 0.23 |
| 0.062M | ref | --- | | | --- | --- | -DIV/0! |
| | bkg | 0.92 | 0.91 | 0.92 | 0.92 | 0.01 | |
| | test | 1.64 | 1.58 | 1.67 | 1.63 | 0.05 | 0.71 |
| 0.125M | ref | --- | | | --- | --- | -DIV/0! |
| | bkg | 0.9 | 0.91 | 0.92 | 0.91 | 0.01 | |
| | test | 1.66 | 1.57 | 1.6 | 1.61 | 0.05 | 0.70 |
| 0.25M | ref | --- | | | --- | --- | -DIV/0! |
| | bkg | 0.92 | 0.93 | 0.9 | 0.92 | 0.02 | |
| | test | 1.65 | 1.65 | 1.72 | 1.67 | 0.04 | 0.76 |
| 0.5M | ref | --- | | | --- | --- | -DIV/0! |
| | bkg | 0.92 | 0.93 | 0.94 | 0.93 | 0.01 | |
| | test | 1.83 | 1.77 | 1.89 | 1.83 | 0.06 | 0.90 |
| 1.0M | ref | --- | | | --- | --- | -DIV/0! |
| | bkg | 0.94 | 0.93 | 0.96 | 0.94 | 0.02 | |
| | test | 1.89 | 1.94 | 1.86 | 1.90 | 0.04 | 0.95 |
| Mg+Ca Chlorides 0 | ref | --- | | | --- | --- | -DIV/0! |
| | bkg | 0.88 | 0.9 | 0.91 | 0.90 | 0.02 | |
| | test | 1.13 | 1.21 | 1.18 | 1.17 | 0.04 | 0.28 |
| 0.062M | ref | --- | | | --- | --- | -DIV/0! |
| | bkg | 0.9 | 0.94 | 0.88 | 0.91 | 0.03 | |
| | test | 1.6 | 1.61 | 1.56 | 1.59 | 0.03 | 0.68 |
| 0.125M | ref | --- | | | --- | --- | -DIV/0! |
| | bkg | 0.9 | 0.91 | 0.93 | 0.91 | 0.02 | |
| | test | 1.7 | 1.67 | 1.65 | 1.67 | 0.03 | 0.76 |

*FIG. 6.*
(1 OF 2)

| | | | | | | | | | |
|---|---|---|---|---|---|---|---|---|---|
| 0.25M | ref | | | | | --- | --- | -DIV/0! | |
| | bkg | 0.9 | 0.93 | 0.91 | | 0.91 | 0.02 | | |
| | test | 1.94 | 1.8 | 1.7 | | 1.81 | 0.12 | 0.90 | |
| 0.5M | ref | | | | | --- | --- | -DIV/0! | |
| | bkg | 0.91 | 0.93 | 0.92 | | 0.92 | 0.01 | | |
| | test | 2.01 | 1.98 | 1.87 | | 1.95 | 0.07 | 1.03 | |
| 1.0M | ref | | | | | --- | --- | -DIV/0! | |
| | bkg | 0.92 | 0.93 | 0.92 | | 0.92 | 0.01 | | |
| | test | 1.89 | 2.02 | 1.98 | | 1.96 | 0.07 | 1.04 | |

*FIG. 6.*
(2 OF 2)

| I.D. | SPOT | DENSITY | | | | | | | | x | S.D. | spot-bkg |
|---|---|---|---|---|---|---|---|---|---|---|---|---|
| 6% PEG in Tris Backbone Diluent | ref | | | | | | | | | --- | --- | -DIV/0! |
| | bkg | 0.9 | 0.89 | 0.91 | 0.9 | 0.9 | 0.9 | 0.89 | 0.91 | 0.90 | 0.01 | |
| | test | 1.74 | 1.69 | 1.73 | 1.92 | 1.78 | 1.9 | 1.80 | 1.79 | 1.79 | 0.08 | 0.89 |
| | ref | | | | | | | | | --- | --- | -DIV/0! |
| | bkg | | | | | | | | | --- | --- | |
| | test | | | | | | | | | --- | --- | -DIV/0! |
| No PEG in Tris Backbone Diluent | ref | | | | | | | | | --- | --- | -DIV/0! |
| | bkg | 0.9 | 0.91 | 0.91 | 0.89 | 0.91 | 0.91 | 0.89 | 0.90 | 0.90 | 0.01 | |
| | test | 1.23 | 1.24 | 1.2 | 1.24 | 1.25 | 1.26 | 1.20 | 1.28 | 1.24 | 0.03 | 0.34 |
| | ref | | | | | | | | | --- | --- | -DIV/0! |
| | bkg | | | | | | | | | --- | --- | |
| | test | | | | | | | | | --- | --- | -DIV/0! |

*FIG. 7.*

| I.D. | SPOT | DENSITY | | | | | | | | | | x | S.D. | spot-bkg |
|---|---|---|---|---|---|---|---|---|---|---|---|---|---|---|
| No Tc-NBT/Men. 1/50, Tris Diluent Std. Substrate | ref | | | | | | | | | | | --- | --- | -DIV/0! |
| | bkg | 0.96 | 0.93 | 0.92 | 0.91 | 0.97 | 0.92 | 0.97 | 0.92 | 0.90 | 0.91 | 0.93 | 0.03 | |
| | test | 1.29 | 1.24 | 1.24 | 1.25 | 1.34 | 1.31 | 1.36 | 1.28 | 1.28 | 1.22 | 1.28 | 0.04 | 0.35 |
| | ref | | | | | | | | | | | --- | --- | |
| | bkg | | | | | | | | | | | --- | --- | |
| | test | | | | | | | | | | | --- | --- | -DIV/0! |
| 50 uM Tc-NBT 1/1000, PEG/MgCl Substrate/LiNO3 | ref | | | | | | | | | | | --- | --- | -DIV/0! |
| | bkg | 0.91 | 0.93 | 0.94 | 0.92 | 0.96 | 0.91 | 0.94 | 0.95 | 0.92 | 0.95 | 0.93 | 0.02 | |
| | test | 1.33 | 1.36 | 1.29 | 1.38 | 1.34 | 1.31 | 1.24 | 1.32 | 1.28 | 1.30 | 1.32 | 0.04 | 0.38 |
| | ref | 0.38/0.35=108% | | | | | | | | | | --- | --- | -DIV/0! |
| | bkg | | | | | | | | | | | --- | --- | |
| | test | | | | | | | | | | | --- | --- | -DIV/0! |

*FIG. 9.*

| I.D. | SPOT | DENSITY | | | | | | | | | | x | S.D. | spot-bkg |
|---|---|---|---|---|---|---|---|---|---|---|---|---|---|---|
| T=0 | ref | | | | | | | | | | | --- | --- | -DIV/0! |
| Lot 249-97A | bkg | 0.93 | 0.91 | 0.94 | 0.92 | 0.91 | 0.93 | 0.95 | | | | 0.93 | 0.01 | |
| No Tc-NBT | test | 1.49 | 1.38 | 1.53 | 1.41 | 1.33 | 1.47 | 1.49 | | | | 1.44 | 0.07 | 0.52 |
| | ref | | | | | | | | | | | --- | --- | -DIV/0! |
| Lot 249-97B | bkg | 0.93 | 0.91 | 0.93 | 0.92 | 0.92 | 0.93 | 0.92 | | | | 0.92 | 0.01 | |
| 50 uM Tc-NBT | test | 1.33 | 1.25 | 1.31 | 1.35 | 1.34 | 1.30 | 1.42 | | | | 1.33 | 0.05 | 0.41 |
| | ref | | | | | | | | | | | --- | --- | |
| | bkg | | | | | | | | | | | --- | --- | |
| | test | | | | | | | | | | | --- | --- | -DIV/0! |
| T=2 Weeks | ref | | | | | | | | | | | --- | --- | -DIV/0! |
| No Tc-NBT | bkg | 0.94 | 0.94 | 0.94 | 0.92 | 0.92 | 0.93 | 0.94 | 0.94 | 0.93 | | 0.93 | 0.01 | |
| 4oC | test | 1.47 | 1.49 | 1.48 | 1.49 | 1.42 | 1.52 | 1.50 | 1.52 | 1.51 | | 1.49 | 0.03 | 0.56 |
| | ref | | | | | | | | | | | --- | --- | -DIV/0! |
| No Tc-NBT | bkg | 0.93 | 0.91 | 0.92 | 0.93 | 0.93 | 0.93 | 0.93 | 0.93 | | | 0.93 | 0.01 | |
| 45oC | test | 1.32 | 1.23 | 1.27 | 1.29 | 1.26 | 1.33 | 1.28 | 1.34 | | | 1.29 | 0.04 | 0.36 |
| T=2 Weeks | ref | | | | | | | | | | | --- | --- | -DIV/0! |
| 50 uM Tc-NBT | bkg | 0.91 | 0.93 | 0.92 | 0.91 | 0.93 | 0.93 | 0.95 | 0.94 | 0.93 | 0.91 | 0.93 | 0.01 | |
| 4oC | test | 1.26 | 1.3 | 1.29 | 1.26 | 1.28 | 1.40 | 1.45 | 1.44 | 1.42 | 1.31 | 1.34 | 0.08 | 0.42 |
| | ref | | | | | | | | | | | --- | --- | -DIV/0! |
| 50 uM Tc-NBT | bkg | 0.91 | 0.93 | 0.92 | 0.93 | 0.93 | 0.94 | 0.91 | 0.91 | 0.91 | 0.92 | 0.92 | 0.01 | |
| 45oC | test | 1.16 | 1.24 | 1.17 | 1.36 | 1.31 | 1.22 | 1.15 | 1.22 | 1.20 | 1.20 | 1.22 | 0.07 | 0.30 |
| | ref | No Tc-NBT: 0.36/0.56=64.3% | | | | | | | | | | --- | --- | -DIV/0! |
| | bkg | 50 uM Tc-NBT: 0.30/0.42=71.4% | | | | | | | | | | --- | --- | |
| | test | | | | | | | | | | | --- | --- | -DIV/0! |
| T=4 Weeks | ref | | | | | | | | | | | --- | --- | -DIV/0! |
| No Tc-NBT | bkg | 0.93 | 0.93 | 0.94 | 0.92 | 0.93 | 0.94 | 0.93 | 0.94 | 0.93 | 0.92 | 0.93 | 0.01 | |
| 4oC | test | 1.33 | 1.51 | 1.62 | 1.46 | 1.53 | 1.55 | 1.47 | 1.47 | 1.62 | 1.41 | 1.50 | 0.09 | 0.57 |
| | ref | | | | | | | | | | | --- | --- | -DIV/0! |
| No Tc-NBT | bkg | 0.93 | 0.93 | 0.92 | 0.94 | 0.92 | 0.93 | 0.94 | 0.93 | 0.93 | 0.94 | 0.93 | 0.01 | |
| 45oC | test | 1.25 | 1.29 | 1.28 | 1.39 | 1.29 | 1.40 | 1.36 | 1.24 | 1.34 | 1.36 | 1.32 | 0.06 | 0.39 |
| T=4 Weeks | ref | | | | | | | | | | | --- | --- | -DIV/0! |
| 50 uM Tc-NBT | bkg | 0.93 | 0.94 | 0.92 | 0.95 | 0.93 | 0.95 | 0.93 | 0.94 | 0.93 | 0.94 | 0.94 | 0.01 | |
| 4oC | test | 1.37 | 1.47 | 1.43 | 1.32 | 1.36 | 1.40 | 1.29 | 1.34 | 1.27 | 1.40 | 1.37 | 0.06 | 0.43 |
| | ref | | | | | | | | | | | --- | --- | -DIV/0! |
| 50 uM Tc-NBT | bkg | 0.93 | 0.93 | 0.94 | 0.93 | 0.94 | 0.94 | 0.94 | 0.92 | 0.94 | 0.95 | 0.94 | 0.01 | |
| 45oC | test | 1.25 | 1.25 | 1.26 | 1.17 | 1.29 | 1.31 | 1.27 | 1.27 | 1.21 | 1.32 | 1.26 | 0.04 | 0.32 |
| | ref | No Tc-NBT: 0.39/0.57=68.4% | | | | | | | | | | --- | --- | -DIV/0! |
| | bkg | 50 uM Tc-NBT: 0.32/0.43=74.4% | | | | | | | | | | --- | --- | |
| | test | | | | | | | | | | | --- | --- | -DIV/0! |

FIG. 8.

STABLE ALKALINE PHOSPHATASE COMPOSITIONS WITH COLOR ENHANCEMENT AND THEIR USE IN ASSAYS

BACKGROUND OF THE INVENTION

The present invention relates generally to the assay of biological specimens. More particularly, it relates to improved compositions and methods for enzyme immunoassays.

An antibody is a protein synthesized by an animal in response to the presence of a foreign substance or antigen. Antibodies, also known as immunoglobulins, have specific affinity for the antigens that elicit their synthesis. Because of the high degree of specificity that antibodies exhibit, the antigen-antibody interaction in vitro is widely used for diagnostic purposes.

Immunoassays (IA), for example, use this specificity to measure the presence of antigens or antibodies in biological samples. Referring to FIGS. 1A-C, the technique is illustrated for a simple monovalent antigen. In FIG. 1A, a membrane having a known receptor (e.g., antibody (Ab)) specific for the molecule of interest is provided. In FIG. 1B, a sample of analyte has been placed on the membrane, and after allowing a sufficient period of time, antigen-antibody complexes (Ag-Ab) form. Any free antigen remaining is separated from the membrane by conventional methods. The amount of antibody sites occupied by antigen is proportional to the amount of antigen present in the sample.

In FIG. 1C, "labeled" antibody (Ab*) is added. "Labeled" antibody, which is conjugated with a moiety that may be easily detected, competes for the same epitope. After allowing sufficient time for the formation of complexes (Ab*-Ag), unbound antibody is removed by conventional methods. The amount of labelled molecules remaining after separation indicates the amount of reaction, and hence the presence (or absence) of a particular analyte. Numerous other assay formats are known and reported in the medical and patent literature.

Several different labels have been employed in IA. Radioimmunoassay (RIA), for example, uses radioactive isotopes as labels. Reaction is detected by the presence of radioactivity.

Enzyme immunoassay techniques, e.g., enzyme-linked immunosorbent assay (ELISA), use antibody or antigen that is conjugated or labelled with an enzyme, for example, alkaline phosphatase. As shown in FIG. 1D, detection of an enzyme-labeled antibody is achieved by the addition of a substrate to the reaction. The enzyme can rapidly convert an added colorless substrate into a color product (e.g., hydrolysis of indoxyl phosphate), or a non-phosphorescent substrate into an intensely fluorescent product. Appearance of a characteristic color that results from the activity of the enzyme on the substrate signifies the presence or absence of analyte.

Because they are less expensive, enzyme immunoassays are rapidly replacing RIA techniques. In addition, special precautions for handling radioactive material are not required. Nevertheless, enzyme immunoassay techniques maintain the high degree of specificity common to immunoassays.

Of particular interest to the present invention is a class of assays referred to as membrane assays. Such assays usually employ a capture antibody or antigen immobilized on a permeable membrane. A sample is applied to and drawn through the membrane, typically by an absorptive layer in contact with the backside of the membrane. The analyte of interest is captured and can be detected by the subsequent application of an enzyme-labeled antibody specific for the analyte.

In large part, immunoassays have been utilized in clinical laboratories to quantitatively determine a wide variety of compounds, particularly drugs and biological markers, such as hormones. Immunoassays have also found less expensive application where semi-quantitative or qualitative results are acceptable, particularly where the determination involves untrained personnel. Even in clinical laboratories though, simple and rapid screening tests shorten lab turnaround time and lower operating costs.

In developing an immunoassay, particular features are desirable. These include, for example, the ease of preparation of the reagents, the accuracy with which samples and reagent solutions must be measured, and the storage stability of the reagents. In developing an assay which could have application with untrained personnel, such as a test to be performed in the home, the observed result should be minimally affected by variations in the reagents used.

Prior techniques, however, employ reagents which are not known for their stability, i.e., the reagents are prone to spontaneous denaturation. For example, the enzyme currently employed in many ELISA and membrane systems, calf intestine alkaline phosphatase (CIAP), is relatively heat labile. Unless it is lyophilized, it is unstable. As a result, it is not available in a convenient form, such as a liquid. The lack of stability of current reagents not only decreases convenience and reliability but also adds to the ultimate cost of the assay as well.

In enzyme immunoassays, it is desirable to have stable reagents which are available in a convenient form. Preferably, the reagents should be economical to produce and be available as a liquid. However, an immunoassay should not be compromised by a reagent which lacks sufficient activity for detection. Thus, it is desirable to employ stable reagents which can be detected, either readily or with enhancement. The present invention fulfills these and other needs.

SUMMARY OF THE INVENTION

Enhanced color development of the present invention permits use of *E. coli* alkaline phosphatase (ECAP), an enzyme with increased stability, in a wide variety of immunoassays, particularly membrane flow-through immunoassays. In accordance with the present invention, lithium salts are combined in a reaction zone with the ECAP conjugate and the substrate, preferably being added as part of the substrate solution. Color enhancement may also be provided by combining Group II salts selected from calcium and magnesium salts in the reaction mixture, preferably being added as part of the ECAP solution. The reaction mixture may be a liquid phase, or in the case of membrane assays, may be a combined solid phase-liquid phase medium, typically comprising immobilized ECAP exposed to liquid phase substrate where a colored reaction product is deposited on the solid phase. Color development is further enhanced by immobilizing tetrazolium dyes, such as the Nitro Blue tetrazolium series, on the membrane.

The present invention finds immediate application with membrane assay technology where analyte, ECAP conjugate, and substrate solutions are sequentially applied to a membrane having immobilized capture receptor (antibody or antigen) for the analyte of interest. The Group II salts are introduced to the reaction zone with the ECAP conjugate and the lithium salt introduced subsequently with the substrate solution. Tetrazolium dye is optionally immobilized on the membrane.

BRIEF DESCRIPTION OF THE DRAWINGS

FIGS. 4–5 display the color enhancement results of samples which were assayed with lithium nitrate at various concentrations and incubation times.

FIG. 6 displays the color enhancement results of samples which were assayed with varying concentrations of calcium chloride and magnesium chloride.

FIG. 7 displays the color enhancement results of sample which were assayed with and without 6% PEG.

FIG. 8 demonstrates the extreme stability of immobilized tetrazolium in a dry form.

FIG. 9 demonstrates that the overall color development activity of the *E. coli* alkaline phosphatase conjugate in enzyme immunoassays can be increased geometrically at least twenty times.

DESCRIPTION OF THE SPECIFIC EMBODIMENTS

Figure 1A:
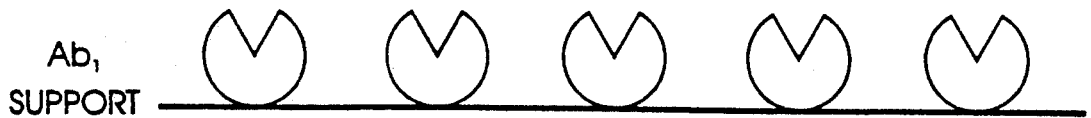
FIG. 1A illustrates a membrane having a known receptor specific for the molecule of interest.
Figure 1B:
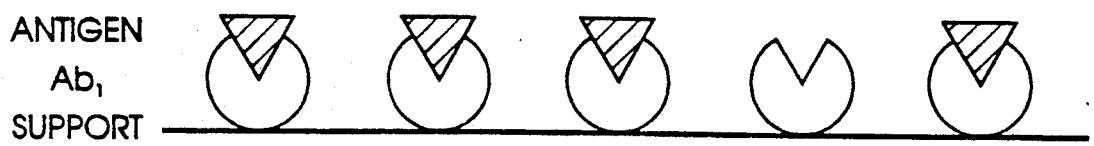
FIG. 1B, illustrates the membrane after a sample of analyte has been placed on it.
Figure 1C:
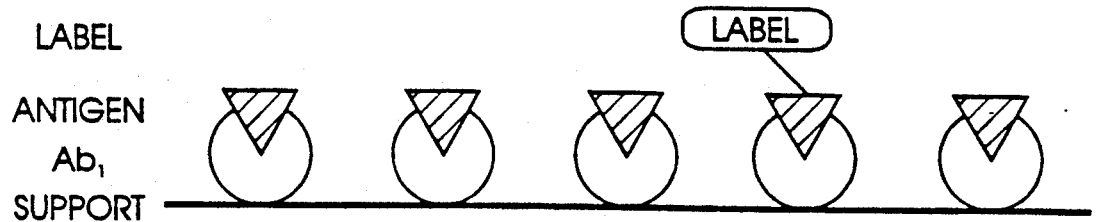
FIG. 1C illustrates the membrane after a "labeled" specific binding substance, e.g., labeled antibody (Ab*), is added.
Figure 1D:
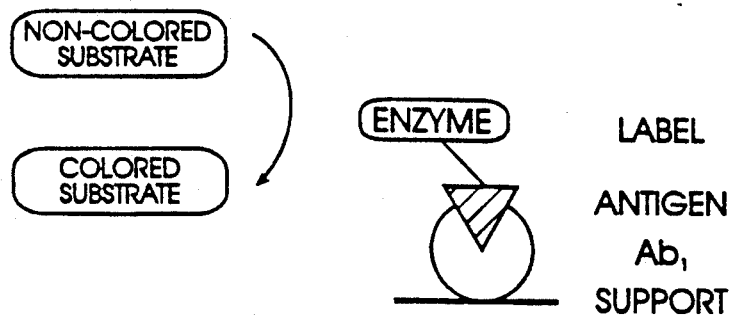
FIG. 1D illustrates the membrane after application of a substrate.

The present invention provides an improved immunoassay for determining the presence of analyte in a sample. In a preferred method of the invention, development of non-colored substrate into a colored product by conjugates of *Escherichia coli* alkaline phosphatase (ECAP) is facilitated by the addition of color enhancers.

Conjugates are specific binding substances which are labeled or conjugated with ECAP. For example, pregnanediol glucosiduronate (PDG) and pregnenolone glucosiduronate (PNG) may be conjugated to ECAP by the active-ester chemistry at the carboxyl end of the glucosiduronate. The preparation of additional ECAP conjugates is disclosed in Japanese Patent No. 52099211, the disclosure of which is hereby incorporated by reference. ECAP conjugates may also be prepared for gene-encoded, protein analytes. See, Lindbladh, C. et al., *The Design of a Simple Competitive ELISA Using Human Proinsulin-Alkaline Phosphatase Conjuates Prepared by Gene Fusion*, Biochemical and Biophysical Research Communications, 149:2, pp. 607–614, 1987, the disclosure of which is hereby incorporated by reference.

A wide variety of assay protocols may be employed, including competitive and non-competitive techniques where the ECAP is combined with color-producing substrate in a reaction zone, and the present invention is not limited to any particular technique. Moreover, the present invention is also compatible with virtually any system employing enzyme labels. The utility of the present invention in immunoassays is limited only by the ability to form conjugates of *E. coli* alkaline phosphatase (ECAP).

1. Materials

In the preferred embodiments, *Escherichia coli* alkaline phosphatase (ECAP) conjugates of pregnanediol glucosiduronate (PDG) and pregnenolone glucosiduronate (PNG) are employed. PDG and PNG are available from Steraloids, Inc., Wilton, NH, Cat. Nos. P6040 and 5520, respectively. ECAP is available from Worthington Co., of Freehold, NJ, Cat. No. BAPF. Reagents required for preparation of the conjugate include N-hydroxysuccinimide (Aldrich Co. of Milwaukee, WI, Cat. No. 13067-2), 1-ethyl-3-(3-dimethylaminopropyl)-carbodiimide hydrochloride (Sigma Co., Cat. No. E7750), and dimethylformamide (Aldrich Co., Cat. No. 15481-4).

The color enhancers include a lithium salt, Group II salts, and polyalcohol polymer. Suitable lithium salts are salts of strong acids, such as lithium chloride, lithium nitrate, and lithium sulfate. However, lithium salts of weaker acids, such as lithium acetate, also yield acceptable results. The Group II salts typically include salts of strong acids, such as chlorides, nitrates, and sulfates of calcium and magnesium.

Substrate suitable for use includes any organophosphate which is readily hydrolyzable from a colorless to colored product, including indoxyl and naphthyl phosphates. The indoxyl phosphates may be selected from the group consisting of bromo-chloro-3-indoxyl phosphate (e.g., 5-bromo-4-chloro-3-indoxyl phosphate) and 3-indoxyl phosphate. In a preferred embodiment, 3-indoxyl phosphate is used.

The color-reaction mixture utilized will depend on the protocol employed. In the preferred embodiment, the following solution is used:

TABLE 1

| Tris base | 30.05 g/l |
|---|---|
| AMP | 17.8 g/l |
| Thimerosal | 0.1 g/l |
| Sodium chloride | 10.0 g/l |
| MgCl$_2$.6H2O | 0.203 g/l |
| 3-Indoxyl phosphate | 3.0 g/l. | titrated to a final pH of about 10.3. Tris base is available from Mallinckrodt of St. Louis, MO, Cat. No. 1806 KBB2. AMP (2-amino-2-methyl-propanol) is available from Aldrich, Cat. No. A6,518-2. 3-indoxyl phosphate AMPD, is available from JBL Scientific of San Luis Obispo, CA, Cat. No. 122-0 C.

The conjugate diluent utilized will also depend on the protocol employed. In the preferred embodiment, the following solution is used:

TABLE 2

| Tris base | 12.11 g/l |
|---|---|
| Tween 20 | 0.4 ml/l |
| Thimerosal | 0.2 g/l |

TABLE 2-continued

| | |
|---|---|
| Sodium azide | 1 g/l |
| MgCl$_2$.6H2O | 0.203 g/l |
| ZnCl$_2$ | 0.0068 g/l. | titrated to a final pH of about 7.4. Tween 20 (polyoxyethylene(20)sorbitans) is available from Aldrich Co., Cat. No. 27434-8.

Tetrazolium dye is selected from the Nitro Blue tetrazolium series, such as nitro blue tetrazolium and thiocarbamyl nitro blue tetrazolium (Tc-NBT) available from Sigma Chemical Co. of St. Louis, MO, Cat. Nos. N-1540-5 and T-7002, respectively.

2. Methods

The preferred embodiments include membrane flow-through assays where the membrane defines the reaction zone, with particularly preferred assays using pregnanediol glucosiduronate (PDG) conjugate of ECAP and anti-PDG.

The PDG (and PNG) conjugate is prepared as follows. Alkaline phosphatase from *Escherichia coli* is centrifuged in a suspension of ammonium sulfate at 12,000×g. and 2°-8° C. for about fifteen to twenty minutes. This yields a pellet of the precipitated enzyme. The supernatant is carefully removed and discarded. An appropriate amount of phosphate buffer saline (PBS) is added to the pellet to bring the total concentration of protein to 20-25 mg/ml. (The coefficient of extinction of alkaline phosphate from *E. coli* is 0.77 at 1 mg/ml.) The enzyme solution is then dialyzed against PBS containing 1 mM MgCl$_2$ (V/V=1/4000) in three changes at 4° C. for two to three days. The dialyzed enzyme is then diluted with PBS containing 1 mM MgCl$_2$ to reach a final concentration of protein of about 7 mg/ml.

About 5.0 to 5.2 mg of PDG (or PNG) is mixed with about 1.3-2.0 mg of N-hydroxysuccinimide and about 4.0-5.0 mg of 1-ethyl-3-(3-dimethylaminopropyl)-carbodiimide hydrochloride in about 0.6 ml dimethylformamide. This is stirred continuously for twenty hours at room temperature in order to prepare the NHS ester of PDG or PNG. An additional 1.4 ml of dimethylformamide is then added to the mixture. About 80 µl of the prepared active ester of PDG or PNG is then added at a rate of 5 µl per minute to 700 µl of the dialyzed enzyme solution (7 mg/ml) at room temperature while stirring vigorously. After four hours of reaction, the mixture is passed through a Sephadex G-25 column (1.5×28.5 cm) that had been equilibrated with 50 mM Tris HCl at a pH of 7.4 containing 100 mM NaCl, 1 mM MgCl$_2$ and 0.01% Tween 20 in order to purify the enzyme conjugate. The resultant conjugate has a molar ratio of PDG/enzyme or PNG/enzyme of about 3:1. The stock conjugate is then properly diluted for use in the assay.

Figure 2A:
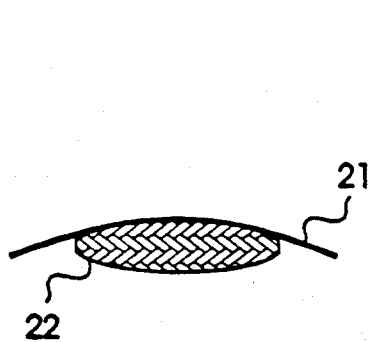
FIG. 2A illustrates a membrane assay in accordance with the principles of the present invention.
Figure 2B:
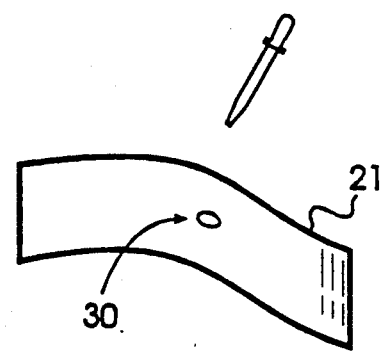
FIG. 2B illustrates the membrane after the application of a spotting solution containing a specific binding substance.

As illustrated in FIG. 2A, the assay includes a membrane 21 with an absorptive layer 22 in contact with the backside of the membrane. Membrane 21 can be any flow-through membrane, for example, a nylon membrane. As seen in FIG. 2B, a spotting solution containing a specific binding substance, such as anti-PDG antibody, is applied to membrane 21 so that specific binding substance is immobilized at a reaction zone or capture area 30 of membrane 21.

Figure 3A:
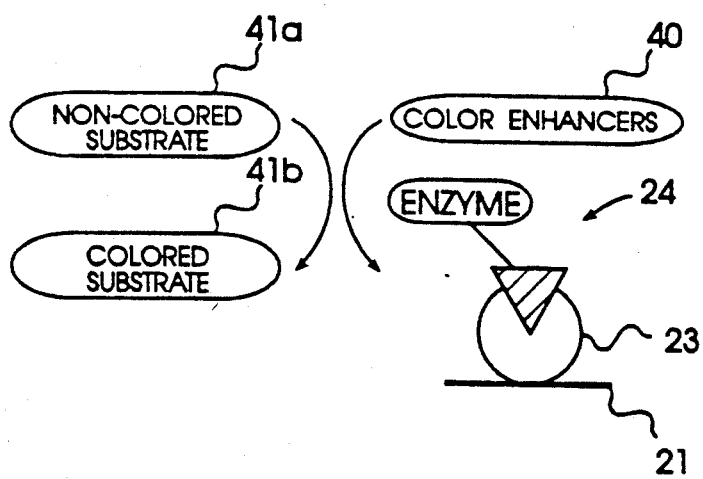
FIG. 3A illustrates the assay of a monovalent analyte in accordance with the principles of the present invention.

Referring to FIG. 3A, the assay of a sample is illustrated. Specific binding substance (receptor) 23, e.g., anti-PDG antibody, is disposed along membrane 21 which is initially unbound. The sample and immobilized anti-PDG antibody are combined in any convenient manner. Anti-PDG/PDG complexes form in proportion to the PDG present in the sample. Unbound PDG is removed by conventional methods. Next, a conjugate, such as ECAP-labeled PDG (ECAP conjugate) 24, is added. The conjugate combines with any unbound anti-PDG. Excess conjugate is removed. Finally, a color-reaction mixture containing substrate solution and color enhancers is added. With the aid of color enhancers 40, previously non-colored substrate 41a is converted by ECAP into a colored product 41b which may be easily detected.

Figure 3B:
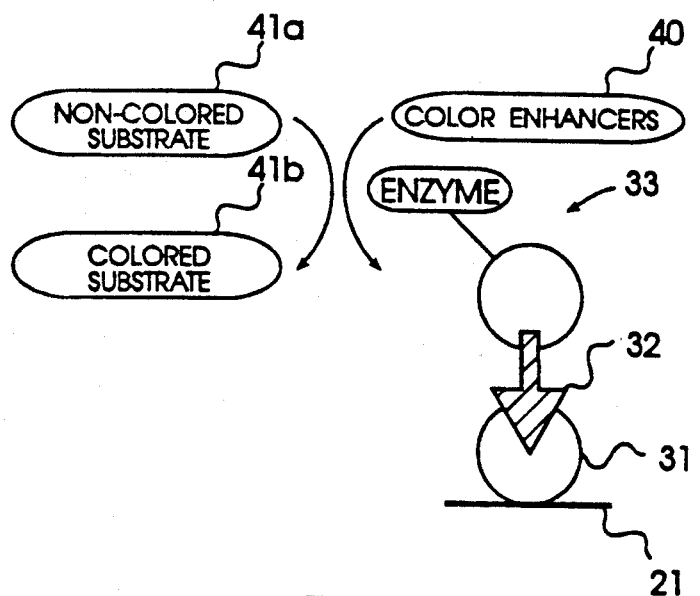
FIG. 3B illustrates the assay of a polyvalent analyte in accordance with the principles of the present invention.

Referring the FIG. 3B, an embodiment for assaying a polyvalent antigen, such as luteinizing hormone (LH), is shown. Anti-LH antibody 31 is immobilized on membrane 21. A sample is applied. LH molecule 32 is captured by anti-LH 31. Labeled anti-LH antibody (conjugate) 33, which is specific for a different LH epitope, is added and binds to captured LH. Non-colored substrate 41a is converted into colored substrate 41b by conjugate 33 and color enhancers 40.

According to the present invention, color enhancers 40 are provided in a color-reaction medium to enhance the color development of the substrate, thereby increasing the sensitivity of the assay. It will be appreciated that each constituent of the color enhancers operates independently of the other to enhance color development. Since enhancement is cumulative, however, maximum enhancement is obtained when all constituents are combined.

Preferably the lithium salt is lithium nitrate, the calcium salt is calcium chloride and the magnesium salt is magnesium chloride, and the polyalcohol polymer is polyethylene glycol. The preferred concentrations are as follows:

TABLE 3

| | Concentration Ranges | | |
|---|---|---|---|
| | Broad | Narrow Range | Preferred |
| Lithium salt | 0.1-2.0 M | 0.5-1.5 M | 1.0 M |
| Calcium salt | 0.1-1.5 M | 0.4-1.0 M | 0.5 M |
| Magnesium salt | 0.1-1.5 M | 0.4-1.0 M | 0.5 M |
| Polyalcohol polymer | 2-10% | 4-8% | 5-6% |

The concentration of conjugate will depend on the desired sensitivity of the assay. For an assay having a sensitivity of 0.5-10 µg/ml for analyte, for example, conjugate is typically at a concentration of about 10-50 µg/ml.

The lithium salt is introduced to the reaction zone contemporaneously with the delivery of the substrate solution. The calcium and/or magnesium salts are introduced to the reaction zone contemporaneously with the delivery of the conjugate. The color enhancers may further include an agent for promoting antigen-antibody binding, such as polyalcohol polymers. The polymer should be introduced to the reaction zone contemporaneously with the delivery of the conjugate.

Addition of tetrazolium dyes further enhances color development. Prior techniques, however, where tetrazolium is mixed with the substrate solution just before use, have several disadvantages. The mixture is cumbersome to prepare and yields an unstable product. Furthermore, as substrate solution and tetrazolium dye are applied together, the dye covers a substantially larger area than the area of interest--the capture area. Subsequent development of the dye beyond the capture area creates a "high background color" which makes it difficult to evaluate color development at the capture area.

Thus, according to the present invention, tetrazolium is employed at a single location. Referring again to FIG. 2B, in a preferred embodiment tetrazolium dye is immobilized at capture site 30 by incorporating it into the spotting antibody solution that is deposited on membrane 21. Once air-dried, both the tetrazolium and the antibody become firmly bound to the membrane. A purple color readily develops at the site when an indoxyl phosphate substrate (e.g., bromo-chloro-3-indoxyl phosphate or 3-indoxyl phosphate) is hydrolyzed. As a result, only tetrazolium dye at the capture site can be converted.

3. Experimental Results

Referring to FIGS. 4-7, membrane flow-through assays were performed using pregnanediol glucosiduronate (PDG) conjugate of ECAP and anti-PDG. In FIGS. 4-5, samples were assayed with lithium nitrate at various concentrations and incubation times. The addition of lithium salts enhanced color development up to five fold.

In FIG. 6, samples were assayed with varying concentrations of calcium chloride and magnesium chloride added to the conjugate diluent (Table 2). It is apparent that the addition of calcium and/or magnesium salts significantly increases color development.

In FIG. 7, samples were assayed with and without 6% PEG in the conjugate diluent (Table 2). The incorporation of polyalcohol polymers nearly triple the intensity of the color development.

By using tetrazolium dyes, the intensity of color, by visual inspection, appears to be enhanced three fold. As seen in FIG. 8, the immobilized tetrazolium in dry form stored at a temperature of 45° C. demonstrates stability at four weeks. Thus, one or more years of stability can be expected with proper storage (sealed, foil pouch) at a room temperature of 25° C.

As seen in FIG. 9, overall color development activity of the E. coli alkaline phosphatase conjugate in enzyme immunoassays is shown. In the first set of data, the membrane is not spotted with Tc-NBT; the enzyme conjugate is diluted 1/50 in the unenhanced buffer solution (Table 2); and the unenhanced substrate solution (Table 1) is used. In the second set of data, the membrane is spotted with 50 $\mu$M of Tc-NBT; the enzyme conjugate is diluted 1/1000 in the buffer solution (Table 2) which is enhanced with 5% PEG and 0.5M magnesium chloride; and the substrate solution (Table 1) is enhanced with 1M of lithium nitrate. The results show that color enhancement can be increased geometrically at least twenty times. Therefore, the cumulative effect of each constituent is demonstrated.

It is apparent from these data that the color enhancers of the present invention substantially increase the color development of substrate by ECAP. Benefits from enhanced development include: 1) ability to use enzyme with greater stability—reagents whose reduced activity prevented their use; 2) economy of reagent—less enzyme conjugate needs to be used per test; 3) speed—a shorter incubation time is needed for the substrate; and 4) higher sensitivity—lower levels of analyte can be detected.

While the invention is described in some detail with specific reference to a single preferred embodiment and certain alternatives, there is no intent to limit the invention to that particular embodiment or those specific alternatives. The true scope of the invention is defined not by the foregoing description but by the following claims.

What is claimed is:

1. In an immunoassay for determining the presence of analyte in a sample, said assay depending on color development of substrate by an enzyme conjugate in a reaction zone, an improvement comprising:
   combining the substrate and a lithium salt with *Escherichia coli* alkaline phosphatase conjugate in the reaction zone.

2. The immunoassay of claim 1, wherein the lithium salt is combined at a concentration from about 0.1 to 2M.

3. The immunoassay of claim 1, wherein said lithium salt is selected from the group consisting of lithium chloride, lithium nitrate, lithium sulfate, and lithium acetate.

4. The immunoassay of claim 1, wherein said lithium salt is lithium nitrate combined at a concentration of about 1M.

5. The immunoassay of claim 1, further comprising combining a polyalcohol polymer with the conjugate in the reaction medium.

6. The immunoassay of claim 5, wherein said polyalcohol polymer is combined at a concentration from about 2% to 10%.

7. The immunoassay of claim 5, wherein said polyalcohol polymer is combined at a concentration from about 4% to 8%.

8. In an immunoassay for determining the presence of analyte in a sample, said assay depending on color development of substrate by an enzyme conjugate in a reaction zone, an improvement comprising:
   combining *Escherichia coli* alkaline phosphatase conjugate with at least one Group II salt.

9. The immunoassay of claim 8, wherein said at least one Group II salt is selected from the group consisting of calcium chloride and magnesium chloride.

10. The immunoassay of claim 8, wherein said at least one Group II salt is at least one of calcium chloride combined at a concentration of about 0.5M and magnesium chloride combined at a concentration of about 0.5M.

11. In an immunoassay for determining the presence of analyte in a sample, said assay depending on color development of substrate by enzyme conjugate, an improvement comprising:
   combining *Escherichia coli* alkaline phosphatase conjugate and a lithium salt with the substrate at a reaction zone;
   combining at least one Group II salt with the conjugate;
   combining a polyalcohol polymer with the conjugate; and
   immobilizing tetrazolium dye at the reaction zone.

12. A method for assaying analyte in a sample comprising:
   (a) applying the sample to a membrane having immobilized receptor for the analyte;
   (b) applying a conjugate of *Escherichia coli* alkaline phosphatase to the membrane; and
   (c) applying a substrate including a lithium salt to the membrane, wherein said substrate is developed into a colored product by said conjugate.

13. The method of claim 12, wherein before step comprises the step:

(e) applying to the membrane at least one Group II salt selected from calcium chloride at a concentration of 0.5M and magnesium chloride at a concentration of 0.5M.

14. The method of claim 12, wherein before step further comprises the step:
(f) applying to the membrane polyethylene glycol a concentration of about 5%.

15. In an immunoassay for determining the presence of analyte in a sample, said assay depending on color development of substrate by enzyme conjugate, an improve comprising:
combining *Escherichia coli* alkaline phosphatase and substrate with lithium nitrate at a concentration of about 1M;
combining with the conjugate at least one of calcium chloride at a concentration of about 0.5M and magnesium chloride at a concentration of about 0.5M;
combining with the conjugate polyethylene glycol a concentration of about 5%; and
immobilizing at the site dye selected from the Nitro Blue tetrazolium series.

16. A method for assaying pregnanediol glucosiduronate (PDG) in a sample comprising:
(a) applying the sample to a membrane having anti-PDG and tetrazolium dye in a reaction zone;
(b) applying a conjugate solution to the membrane, said conjugate solution including a PDG conjugate of *Escherichia coli* alkaline phosphatase, calcium chloride at a concentration of about 0.5M, magnesium chloride at a concentration of about 0.5M, and polyethylene glycol at a concentration of about 5%; and
(c) applying a substrate solution to the membrane, said substrate solution including lithium nitrate at a concentration of about 1M, whereby said substrate solution is developed into a colored product by said conjugate.

17. The method of claim 16, wherein said substrate solution further includes an indoxyl phosphate selected from the group consisting of bromo-chloro-3-indoxyl phosphate and 3-indoxyl phosphate.

18. A method for assaying luteinizing hormone in a sample comprising:
(a) applying the sample to a membrane having a first anti-LH antibody and tetrazolium dye;
(b) applying a conjugate solution to the membrane, said conjugate solution including a second anti-LH antibody, calcium chloride at a concentration of about 0.5M, magnesium chloride at a concentration of about 0.5M, and polyethylene glycol at a concentration of about 5%, wherein said second anti-LH antibody is a conjugate of *Escherichia coli* alkaline phosphatase; and
(c) applying a substrate solution to the membrane, said substrate solution including lithium nitrate at a concentration of about 1M, whereby said substrate solution is developed into a colored product by said conjugate.

19. The method of claim 18, wherein said substrate solution further includes an indoxyl phosphate selected from the group consisting of bromo-chloro-3-indoxyl phosphate and 3-indoxyl phosphate.

* * * * *